(12) United States Patent
Yeh

(10) Patent No.: US 7,084,264 B2
(45) Date of Patent: Aug. 1, 2006

(54) VIRAL SEQUENCES

(76) Inventor: Chau-Ting Yeh, Liver Research Unit, Chang Gung Memorial Hospital, 199 Tung Hwa North Road, Taipei (TW) 105

(*) Notice: Subject to any disclaimer, the term of this patent is extended or adjusted under 35 U.S.C. 154(b) by 0 days.

(21) Appl. No.: 10/881,758

(22) Filed: Jun. 30, 2004

(65) Prior Publication Data

US 2005/0037399 A1    Feb. 17, 2005

Related U.S. Application Data

(60) Provisional application No. 60/487,672, filed on Jul. 16, 2003.

(51) Int. Cl.
*C12P 19/36* (2006.01)
*C12P 19/34* (2006.01)
*C12P 19/38* (2006.01)
*C12P 19/39* (2006.01)
*C12P 19/02* (2006.01)

(52) U.S. Cl. ............... 536/23.1; 536/24.3; 536/24.31; 536/24.32; 536/24.33; 435/69.1; 435/90; 435/40.5; 435/4; 435/6; 435/91.2; 435/89; 435/90.1; 514/44

(58) Field of Classification Search ............... 536/23.1, 536/23.4, 23.31, 23.41, 23.5, 24.3, 24.31, 536/24.32; 514/44; 435/4, 6, 40.5, 89, 90, 435/91.1, 91.2

See application file for complete search history.

(56) References Cited

OTHER PUBLICATIONS

Tockman et al Cancer Res., 1992, 52:2711s-2718s.*
Rosenberg et al. Nature Medicine 2004, vol. 10, No. 9, pp. 909-915.*
Bae et al. Mol. Cells, 1996, vol. 6, No. 1, pp. 101-107.*
Maggiore et al. RAY, 2004, vol. 29, No. 4, pp. 353-355.*

* cited by examiner

*Primary Examiner*—Bao Qun Li
(74) *Attorney, Agent, or Firm*—Fish & Richardson P.C.

(57) ABSTRACT

An isolated nucleic acid comprising the nucleotide sequence of SEQ ID NO:1, or the full complementary sequence thereof. Presence of said nucleic acid in a subject predisposes the subject to an adenocarcinoma. Also disclosed are a method of diagnosing an adenocarcinoma.

4 Claims, No Drawings

SEQUENCE LISTING

<160> NUMBER OF SEQ ID NOS: 5

<210> SEQ ID NO 1
<211> LENGTH: 509
<212> TYPE: DNA
<213> ORGANISM: Homo sapiens
<220> FEATURE:
<221> NAME/KEY: CDS
<222> LOCATION: (1)...(348)

<400> SEQUENCE: 1

```
cca gag ttc ttt ctg cgc cag gtg aag gag ttg cat acg aaa ctg gga      48
Pro Glu Phe Phe Leu Arg Gln Val Lys Glu Leu His Thr Lys Leu Gly
  1               5                  10                  15 gac ttg gag aaa caa ttc ttg gct gtc gac cag ctg aag gag aac aca      96
Asp Leu Glu Lys Gln Phe Leu Ala Val Asp Gln Leu Lys Glu Asn Thr
             20                  25                  30 gcg gaa tta gcc gac tcg aac agc gtg aag atg gag ctg cag cat cta     144
Ala Glu Leu Ala Asp Ser Asn Ser Val Lys Met Glu Leu Gln His Leu
         35                  40                  45 cta agg gag ggt gat gga gaa cga ttg cag aag gca gag aga gtt ctg     192
Leu Arg Glu Gly Asp Gly Glu Arg Leu Gln Lys Ala Glu Arg Val Leu
     50                  55                  60 gag aag gct ctc atg cga atg tat cgg acc ctc ctg atg att gat aat     240
Glu Lys Ala Leu Met Arg Met Tyr Arg Thr Leu Leu Met Ile Asp Asn
 65                  70                  75                  80 ttt gcc aag ctg aac atg gct acc gcg caa cag gtg cag tct cac tgc     288
Phe Ala Lys Leu Asn Met Ala Thr Ala Gln Gln Val Gln Ser His Cys
                 85                  90                  95 act cac ttc att aat tct ttt ttc tac aaa ccg gta ttt tgt gta gat     336
Thr His Phe Ile Asn Ser Phe Phe Tyr Lys Pro Val Phe Cys Val Asp
                100                 105                 110 act cca gaa aca tgacgaggtg tctcccttca aaggggggga tgataccttc         388
Thr Pro Glu Thr
            115 atggcattcc tgttggaaag gcctctcagt gattatcctc ccttgacaga tctcatccaa   448 cggacacagg caaatacatt tccccacccc cccccaaaat gactcacatc aaatcaaacc   508 c                                                                   509
```

<210> SEQ ID NO 2
<211> LENGTH: 116
<212> TYPE: PRT
<213> ORGANISM: Homo sapiens

<400> SEQUENCE: 2

```
Pro Glu Phe Phe Leu Arg Gln Val Lys Glu Leu His Thr Lys Leu Gly
  1               5                  10                  15

Asp Leu Glu Lys Gln Phe Leu Ala Val Asp Gln Leu Lys Glu Asn Thr
             20                  25                  30

Ala Glu Leu Ala Asp Ser Asn Ser Val Lys Met Glu Leu Gln His Leu
         35                  40                  45

Leu Arg Glu Gly Asp Gly Glu Arg Leu Gln Lys Ala Glu Arg Val Leu
     50                  55                  60
```

-continued

```
Glu Lys Ala Leu Met Arg Met Tyr Arg Thr Leu Leu Met Ile Asp Asn
 65              70                  75                  80

Phe Ala Lys Leu Asn Met Ala Thr Ala Gln Gln Val Gln Ser His Cys
             85                  90                  95

Thr His Phe Ile Asn Ser Phe Phe Tyr Lys Pro Val Phe Cys Val Asp
                100                 105                 110

Thr Pro Glu Thr
        115

<210> SEQ ID NO 3
<211> LENGTH: 10
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 7-10
<223> OTHER INFORMATION: n = a, t, c or g

<400> SEQUENCE: 3 ccgcggnnnn                                                                  10

<210> SEQ ID NO 4
<211> LENGTH: 10
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 7-10
<223> OTHER INFORMATION: n = a, t, c or g

<400> SEQUENCE: 4 gaattcnnnn                                                                  10

<210> SEQ ID NO 5
<211> LENGTH: 34
<212> TYPE: DNA
<213> ORGANISM: Artificial Sequence
<220> FEATURE:
<223> OTHER INFORMATION: Primer

<400> SEQUENCE: 5
gcttgctctg tctctttttt ttttttttt tttt                                        34
```

VIRAL SEQUENCES

RELATED APPLICATION

This application claims priority to U.S. Provisional Application Ser. No. 60/487,672, filed Jul. 16, 2003, the contents of which are incorporated herein by reference.

BACKGROUND

Colon cancer is generally believed to be caused by alteration of genetic background with progressive accumulation of somatic chromosomal mutations. However, many human cancers are causatively related to both host genetic factors and environmental factors including viruses. Therefore, it is also possible that a yet unrecognized virus contributes to the oncogensis of colon cancer.

SUMMARY

This invention relates to a novel nucleotide sequence found to be present in a subject with an adenocarcinoma at a frequency higher than that for a normal subject. This nucleotide sequence (designated as "Colon-V;" SEQ ID NO:1) is shown below:

```
  1 ccagagttctttctgcgccaggtgaaggagttgcatacgaaactgggagacttggagaaa
    P  E  F  F  L  R  Q  V  K  E  L  H  T  K  L  G  D  L  E  K 61 caattcttggctgtcgaccagctgaaggagaacacagcggaattagccgactcgaacagc
    Q  F  L  A  V  D  Q  L  K  E  N  T  A  E  L  A  D  S  N  S 121 gtgaagatggagctgcagcatctactaagggagggtgatggagaacgattgcagaaggca
    V  K  M  E  L  Q  H  L  L  R  E  G  D  G  E  R  L  Q  K  A 181 gagagagttctggagaaggctctcatgcgaatgtatcggaccctcctgatgattgataat
    E  R  V  L  E  K  A  L  M  R  M  Y  R  T  L  L  M  I  D  N 241 tttgccaagctgaacatggctaccgcgcaacaggtgcagtctcactgcactcacttcatt
    F  A  K  L  N  M  A  T  A  Q  Q  V  Q  S  H  C  T  H  F  I 301 aattcttttttctacaaaccggtattttgtgtagatactccagaaacatgacgaggtgtc
    N  S  F  F  Y  K  P  V  F  C  V  D  T  P  E  T  *  (SEQ ID NO:2)

361 tcccttcaaaagggggatgataccttcatggcattcctgttggaaaggcctctcagtga 421 ttatcctcccttgacagatctcatccaacggacacaggcaaatacatttccccaccccc 481 cccaaaatgactcacatcaaatcaaaccc (SEQ ID NO:1)
```

The nucleic acid of SEQ ID NO:1 contains an incomplete open reading frame that has 116 amino acids. The amino acid sequence encoded by SEQ ID NO:1 is designated as SEQ ID NO:2.

Accordingly, the invention features an isolated nucleic acid containing a nucleotide sequence at least 70% identical to SEQ ID NO:1, or a complementary sequence thereof. The percent identity can be anywhere between and including 70% and 100%, e.g., 75%, 80%, 85%, 90%, and 95%. Presence of the nucleic acid in a subject predisposes the subject to an adenocarcinoma (e.g., colon cancer, gastric cancer, pancreas cancer, ovarian cancer, breast cancer, lung cancer, and esophageal cancer). A nucleic acid of the invention can be used as a DNA vaccine for treating such a disease.

An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

The "percent identity" of two sequences is determined using the algorithm of Karlin and Altschul ((1990) Proc. Natl. Acad. Sci. USA 87, 2264–2268), modified as in Karlin and Altschul ((1993) Proc. Natl. Acad. Sci. USA 90, 5873–5877). Such an algorithm is incorporated into the XBLAST programs of Altschul et al. ((1990) J. Mol. Biol. 215, 403–410). BLAST searches are performed with the XBLAST program, score=50, wordlength=3. Where gaps exist between two sequences, Gapped BLAST is utilized as described in Altschul et al. ((1997) Nucleic Acids Res. 25, 3389–3402). When utilizing BLAST and Gapped BLAST programs, the default parameters of the respective programs (e.g., XBLAST) are used. See the World Wide Web at ncbi.nlm.nih.gov.

The invention also features a pure polypeptide containing an amino acid sequence encoded by a nucleic acid of the invention. A polypeptide of the invention can be used as a protein vaccine for treating an adenocarcinoma. It can also be used for producing antibodies (either monoclonal or polyclonal) against a polypeptide of the invention. These antibodies in turn are useful for detecting the presence and distribution of the polypeptide in tissues and in cellular compartments. For example, such antibodies can be used to verify the expression of the polypeptide in a transgenic animal.

A "pure polypeptide" refers to a polypeptide substantially free from naturally associated molecules, i.e., it is at least 75% (i.e., anywhere between and including 75% and 100%, e.g., 80%, 85%, 90%, or 95%) pure by dry weight. Purity can be measured by any appropriate standard method, for example, by column chromatography, polyacrylamide gel electrophoresis, or HPLC analysis.

The invention further features an isolated nucleic acid characterized in that it hybridizes under stringent conditions to SEQ ID NO:1, or a complementary sequence thereof, as well as a cell (in a culture or in a transgenic animal) containing a nucleic acid of the invention. Such a nucleic acid can be at least 15 (e.g., at least 30, 50, 100, 200, 500, or 1000) nucleotides in length. An example of a nucleic acid within the invention is an isolated nucleic acid (e.g., a vector) encoding a polypeptide of the invention. These nucleic acids and cells can be used for producing the polypeptides of the invention or generating a transgenic animal. The nucleic acids can also be used as primers in detection methods based on PCR or primer extension, or as labeled probes in nucleic acid blots (e.g., Northern blots).

By hybridization under "stringent conditions" is meant hybridization at 65° C., 0.5×SSC, followed by washing at 45° C., 0.1×SSC.

In addition, the invention features a method of (1) expressing in a cell a transcript, i.e., transcript I, that hybridizes under above-described stringent conditions to SEQ ID NO:1, or (2) expressing in a cell a transcript, i.e., transcript II, that is complementary to transcript I. Transcript I, when expressed in a cell, can serve as an anti-sense RNA that binds to endogenous Colon-V mRNA to prevent it from being translated into a functional protein. Therefore, this method can be used in gene therapy for treating an adenocarcinoma. Transcript II can encode a Colon-V protein, and when expressed in a cell, is translated into a Colon-V protein. Thus, this method can be used for producing a polypeptide of the invention.

Colon-V has been found to be present at a higher than normal frequency in subjects with colon cancer. It is thus useful for diagnosing and treating such a disease.

In one aspect, this invention features a method of determining whether a subject is suffering from or at risk for developing an adenocarcinoma. The method involves providing a sample from a subject and detecting in the sample a nucleic acid containing SEQ ID NO:1, a transcript thereof, or a polypeptide containing SEQ ID NO:2. Presence of the nucleic acid, the transcript, or the polypeptide in the sample indicates that the subject is suffering from or at risk for developing an adenocarcinoma. The nucleic acid, the transcript, and the polypeptide can be detected, e.g., by PCR, Northern blot, and Western blot, respectively, or by any other methods known in the art.

In another aspect, this invention features a method of identifying a compound for preventing and treating an adenocarcinoma. The method involves contacting a compound with a cell having a nucleic acid that contains SEQ ID NO:1, a transcript thereof, or a polypeptide that contains SEQ ID NO:2, and determining a level of the nucleic acid, the transcript, or the polypeptide in the cell. If the level of the nucleic acid, the transcript, or the polypeptide in the presence of the compound is lower than that in the absence of the compound, it indicates the compound is a candidate for treating an adenocarcinoma. Production of a compound thus identified is also within the scope of the invention.

In still another aspect, this invention features a method of treating an adenocarcinoma. The method involves identifying a subject suffering from or being at risk for developing an adenocarcinoma and having a nucleic acid that contains SEQ ID NO:1, a transcript thereof, or a polypeptide that contains SEQ ID NO:2, and administering to the subject an effective amount of a composition to decrease the level of the nucleic acid, the transcript, or the polypeptide in the subject. "Treatment of an adenocarcinoma" herein refers to administering a composition to a subject, who has an adenocarcinoma, a symptom of such a disease or a predisposition towards such a disease, with the purpose to cure, relieve, alter, affect, or prevent the adenocarcinoma, the symptom of it, or the predisposition towards it.

Also within the scope of this invention is a pharmaceutical composition for treating an adenocarcinoma. The composition can contain a pharmaceutically acceptable carrier and a nucleic acid encoding a transcript (i.e., an anti-sense RNA) characterized in that it hybridizes under stringent conditions to SEQ ID NO:1 or an antibody against the polypeptide of SEQ ID NO:2.

The details of one or more embodiments of the invention are set forth in the accompanying description below. Other features, objects, and advantages of the invention will be apparent from the detailed description, and from the claims.

DETAILED DESCRIPTION

This invention is based on the discovery of a novel nucleotide sequence (Colon-V) in a patient with non-A-E hepatitis and colon cancer. The sequence is not present in the human chromosome. Unexpectedly, Colon-V was detected in 4% of healthy individuals and in 0%, 3%, 0%, and 25% of patients with chronic non-A-E hepatitis, chronic hepatitis B, chronic hepatitis C, and colon cancer, respectively. Colon-V was found to be resistant to RNase A digestion but sensitive to DNase I digestion. CsCl gradient analysis showed that Colon-V was present in particles with buoyant densities of about 1.23–1.26 and 1.18 g/ml. These results indicate that Colon-V is a DNA virus associated with an adenocarcinoma, e.g., colon cancer.

In one aspect, the present invention features Colon-V nucleic acids (i.e., DNA, cDNA, and RNA) characterized in that they hybridize under stringent conditions to SEQ ID NO:1, or a complementary sequence thereof. Examples of Colon-V nucleic acids include those containing a nucleotide sequence at least 70% identical to SEQ ID NO:1, or a complementary sequence thereof. Presence of these nucleic acids in a subject predisposes the subject to an adenocarcinoma.

In another aspect, the invention features pure Colon-V polypeptides (e.g., SEQ ID NO:2) encoded by the above-described Colon-V nucleic acids, including functional Colon-V polypeptides. A "functional polypeptide" refers to a polypeptide which possesses biological activity equivalent to that of a wild-type Colon-V protein, e.g., a fragment of a wild-type Colon-V protein.

A nucleic acid of the invention can be expressed in vitro by DNA transfer into a suitable host cell by methods known in the art. For example, the nucleic acid can be inserted into a recombinant expression vector. A variety of host-expression vector systems can be utilized to express a nucleic acid of the invention. These include, but are not limited to, microorganisms such as bacteria transformed with recombinant bacteriophage DNA, plasmid DNA, or cosmid DNA expression vectors; yeast transformed with recombinant yeast expression vectors; and human cell lines infected with recombinant virus or plasmid expression vectors. Isolation and purification of recombinant polypeptides, or fragments thereof, provided by the invention, can be carried out by conventional means including preparative chromatography and immunological separations involving monoclonal or polyclonal antibodies.

The invention also features antibodies against Colon-V polypeptide, including monoclonal antibodies and polyclonal antibodies. The term "antibody" includes intact molecules as well as fragments thereof, such as Fab, F(ab')$_2$, and Fv which are capable of binding to an epitopic determinant present in the Colon-V polypeptide. Methods of making monoclonal and polyclonal antibodies and fragments thereof are known in the art. See, for example, Harlow and Lane (1988) Antibodies: A Laboratory Manual, Cold Spring Harbor Laboratory, New York.

In addition, the invention provides methods for diagnosing and treating an adenocarcinoma, and identifying therapeutic compounds for treating such a disease using Colon-V nucleic acids and polypeptides.

A diagnostic method of this invention involves detecting Colon-V DNA, mRNA, or protein in a sample prepared from a subject. Presence of the Colon-V DNA, mRNA, or protein indicates that the subject is suffering from or at risk for developing an adenocarcinoma. The methods of this invention can be used on their own or in conjunction with other procedures to diagnose an adenocarcinoma in appropriate subjects.

The Colon-V DNA sequence can be detected by a variety of methods known in the art. For example, it can be identified by PCR amplification or Southern blot analysis of genomic DNA prepared from a test sample.

Methods of detecting an mRNA molecule in a sample are known in the art. In order to measure mRNA levels, cells can be lysed and the levels of Colon-V mRNA in the lysates or in RNA purified or semi-purified from the lysates can be determined by any of a variety of methods including, without limitation, hybridization assays using detectably labeled Colon-V-specific DNA or RNA probes and quantitative or semi-quantitative RT-PCR methodologies using appropriate Colon-V-specific oligonucleotide primers. Alternatively, quantitative or semi-quantitative in situ hybridization assays can be carried out using, for example, tissue sections or unlysed cell suspensions, and detectably (e.g., fluorescently or enzyme) labeled DNA or RNA probes. Additional methods for quantifying mRNA include RNA protection assay (RPA) and SAGE.

Methods of detecting a protein in a sample are also known in the art. Many such methods employ antibodies (e.g., monoclonal or polyclonal antibodies) that bind specifically to the Colon-V protein. In such assays, the antibody itself or a secondary antibody that binds to it can be detectably labeled. Alternatively, the antibody can be conjugated with biotin, and detectably labeled avidin (a polypeptide that binds to biotin) can be used to detect the presence of the biotinylated antibody. Combinations of these approaches (including "multi-layer sandwich" assays) familiar to those in the art can be used to enhance the sensitivity of the methodologies. Some of these protein-measuring assays (e.g., ELISA or Western blot) can be applied to lysates of cells, and others (e.g., immunohistological methods or fluorescence flow cytometry) applied to histological sections or unlysed cell suspensions. Methods of measuring the amount of label depend on the nature of the label and are well known in the art. Appropriate labels include, without limitation, radionuclides (e.g., $^{125}$I, $^{131}$I, $^{35}$S, $^{3}$H, or $^{32}$P), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). Other applicable assays include quantitative immunoprecipitation or complement fixation assays.

The invention also provides a method for identifying and manufacturing compounds (e.g., proteins, peptides, peptidomimetics, peptoids, antibodies, or small molecules) that reduce the level of Colon-V DNA, mRNA, or protein in a cell. Compounds thus identified can be used, e.g., for treating an adenocarcinoma.

The candidate compounds of the present invention can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation); spatially addressable parallel solid phase or solution phase libraries; synthetic libraries obtained by deconvolution or affinity chromatography selection; and the "one-bead one-compound" libraries. See, e.g., Zuckermann et al. (1994) J. Med. Chem. 37, 2678–85; and Lam (1997) Anticancer Drug Des. 12, 145.

Examples of methods for the synthesis of molecular libraries can be found in the art, for example, in: DeWitt et al. (1993) PNAS USA 90, 6909; Erb et al. (1994) PNAS USA 91, 11422; Zuckermann et al. (1994) J. Med. Chem. 37, 2678; Cho et al. (1993) Science 261, 1303; Carrell et al. (1994) Angew. Chem. Int. Ed. Engl. 33, 2059; Carell et al. (1994) Angew. Chem. Int. Ed. Engl. 33, 2061; and Gallop et al. (1994) J. Med. Chem. 37, 1233.

Libraries of compounds may be presented in solution (e.g., Houghten (1992) Biotechniques 13, 412–421), or on beads (Lam (1991) Nature 354, 82–84), chips (Fodor (1993) Nature 364, 555–556), bacteria (Ladner, U.S. Pat. No. 5,223,409), spores (Ladner, U.S. Pat. No. 5,223,409), plasmids (Cull et al. (1992) PNAS USA 89, 1865–1869), or phages (Scott and Smith (1990) Science 249, 386–390; Devlin (1990) Science 249, 404–406; Cwirla et al. (1990) PNAS USA 87, 6378–6382; Felici (1991) J. Mol. Biol. 222, 301–310; and Ladner supra).

To identify compounds that reduce the level of Colon-V DNA, mRNA, or protein in a cell, a cell is contacted with a candidate compound and the level of the Colon-V DNA, mRNA, or protein is evaluated relative to that in the absence of the candidate compound. The cell can be a cell that contains the Colon-V sequence yet does not naturally expresses it, a cell that naturally expresses Colon-V, or a cell that is modified to express a recombinant nucleic acid, for example, having the Colon-V sequence fused to a marker gene. The level of the Colon-V or the marker DNA, mRNA, or protein can be determined by methods described above and any other methods well known in the art. If the level of the Colon-V or the marker DNA, mRNA, or protein is lower in the presence of the candidate compound than that in the absence of the candidate compound, the candidate compound is identified as a potential drug for treating an adenocarcinoma.

This invention also provides a method for treating an adenocarcinoma. Subjects to be treated can be identified, for example, by detecting Colon-V DNA, mRNA, or protein in a sample prepared from a subject by methods described above. If the Colon-V DNA, mRNA, or protein is present in the sample, the subject is a candidate for treatment with an effective amount of a compound that reduces the level of Colon-V DNA, mRNA, or protein in the subject. This method can be performed alone or in conjunction with other drugs or therapy.

In one in vivo approach, a therapeutic composition (e.g., a composition containing a compound that reduces the level of Colon-V DNA, mRNA, or protein in a cell) is administered to the subject. Generally, the compound will be suspended in a pharmaceutically acceptable carrier (e.g., physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily.

The dosage required depends on the choice of the route of administration; the nature of the formulation; the nature of the subject's illness; the subject's size, weight, surface area, age, and sex; other drugs being administered; and the judgment of the attending physician. Suitable dosages are in the range of 0.01–100.0 mg/kg. Wide variations in the needed dosage are to be expected in view of the variety of compounds available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery, particularly for oral delivery.

Alternatively, a polynucleotide containing a nucleic acid sequence encoding an anti-sense Colon-V RNA can be delivered to the subject, for example, by the use of polymeric, biodegradable microparticle or microcapsule delivery devices known in the art.

Another way to achieve uptake of the nucleic acid is using liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano et al. (1995) J. Mol. Med. 73, 479). Alternatively, tissue specific targeting can be achieved by the use of tissue-specific transcriptional regulatory elements (TRE) which are known in the art. Delivery of "naked DNA" (i.e., without a delivery vehicle) to an intramuscular, intradermal, or subcutaneous site is another means to achieve in vivo expression.

In the relevant polynucleotides (e.g., expression vectors), the nucleic acid sequence encoding an anti-sense Colon-V RNA is operatively linked to a promoter or enhancer-promoter combination. Enhancers provide expression specificity in terms of time, location, and level. Unlike a promoter, an enhancer can function when located at variable distances from the transcription initiation site, provided a promoter is present. An enhancer can also be located downstream of the transcription initiation site.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles that are suitable for administration to a human, e.g., physiological saline or liposomes. A therapeutically effective amount is an amount of the polynucleotide that is capable of producing a medically desirable result (e.g., a reduced level of Colon-V DNA, mRNA, or protein) in a treated subject. As is well known in the medical arts, the dosage for any one subject depends upon many factors, including the subject's size, body surface area, age, the particular compound to be administered, sex, time and route of administration, general health, and other drugs being administered concurrently. Dosages will vary, but a preferred dosage for administration of polynucleotide is from approximately $10^6$ to $10^{12}$ copies of the polynucleotide molecule. This dose can be repeatedly administered, as needed. Routes of administration can be any of those listed above.

The present invention further features a pharmaceutical composition that contains a pharmaceutically acceptable carrier and an effective amount of a compound that reduces the level of Colon-V DNA, mRNA, or protein in the subject. For example, the compound can be a nucleic acid encoding a transcript characterized in that it hybridizes under stringent conditions to SEQ ID NO:1, or an antibody against the polypeptide of SEQ ID NO:2. The pharmaceutical composition can be used to treat an adenocarcinoma.

The pharmaceutically acceptable carrier includes a solvent, a dispersion medium, a coating, an antibacterial and antifungal agent, and an isotonic and absorption delaying agent. An "effective amount" is the amount required to confer therapeutic effect. The interrelationship of dosages for animals and humans (based on milligrams per meter squared of body surface) is described by Freireich et al. (1966) Cancer Chemother. Rep. 50, 219. Body surface area can be approximately determined from height and weight of the subject. See, e.g., p 537, Scientific Tables, Geigy Pharmaceuticals, Ardley, N.Y., 1970. Effective doses also vary, as recognized by those skilled in the art, dependent on route of administration, excipient usage, and the like.

A pharmaceutical composition of the invention can be formulated into dosage forms for different administration routes utilizing conventional methods. For example, it can be formulated in a capsule, a gel seal, or a tablet for oral administration. Capsules can contain any standard pharmaceutically acceptable materials such as gelatin or cellulose. Tablets can be formulated in accordance with conventional procedures by compressing chitosan with a solid carrier and a lubricant. Examples of solid carriers include starch and sugar bentonite. A pharmaceutical composition of the invention can also be administered in a form of a hard shell tablet or a capsule containing a binder, e.g., lactose or mannitol, a conventional filler, and a tableting agent. The pharmaceutical composition can be administered via the parenteral route. Examples of parenteral dosage forms include aqueous solutions, isotonic saline or 5% glucose of the active agent, or other well-known pharmaceutically acceptable excipient. Cyclodextrins, or other solubilizing agents well known to those familiar with the art, can be utilized as pharmaceutical excipients for delivery of the therapeutic agent.

The efficacy of a pharmaceutical composition of the invention can be evaluated both in vitro and in vivo. Briefly, the composition can be tested in vitro for its ability to reduce the level of Colon-V DNA, mRNA, or protein in a cell. For in vivo studies, the composition can be injected into an animal and its inhibitory effects on an adenocarcinoma are then accessed. Based on the results, an appropriate dosage range and administration route can be determined.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

Materials and Methods

1. Patients

A 66 years old male (Patient-L) suffered from colon cancer (adenocarcinoma in transverse colon). He received colectomy which was subsequently complicated with anastomosis leakage, sepsis, and gastric ulcer bleeding. After treatment, the patient's conditions were stabilized. Unfortunately, an episode of acute hepatitis (peak GPT 284 U/L) with deep jaundice (bilirubin 19 mg/ml) occurred. However, no known viral markers were detected. Two novel viral sequences (NV-F and Colon-V) were later identified in serum obtained from this patient. The study of Colon-V sequence was described in this application.

Serum samples from 5 groups of other subjects were used for Colon-V screening assay. These subjects include 150 normal people (from Health Examination Center) with normal GPT and no identifiable HBV or HCV markers, 50 patients with chronic hepatitis B, 50 patients with chronic hepatitis C, 30 patients with biopsy-proved colon cancer, and 68 patients with chronic non-A-E hepatitis.

2. Serological Study

Hepatitis B surface antigen (HBsAg), total or immunoglobulin M class serum antibody to hepatitis A virus (anti-HAV), and serum antibody to hepatitis D virus (anti-HDV) were assayed using radioimmunoassay kits (Ausria-II, HAVAB or HAVAB-M, and Anti-Delta; Abbott Laboratories, North Chicago, Ill.). Antibody to hepatitis C virus was detected using an enzyme immunoassay kit (HCV-II; Abbott Laboratories, North Chicago, Ill.). HCV-RNA was detected by an RT-PCR assay (Amplicor® HCV test; Roche Diagnostic System, Inc., Branchburg, N.J.). HBV-DNA was detected according to a published method (Yeh et al. (2000) Hepatology 31, 1318).

3. Amplification of Serum DNA

Three primers were synthesized: P1, CCGCGG(N)$_4$ (SEQ ID NO:3); P2, GAATTC(N)$_4$ (SEQ ID NO:4); and P3, GCTTGCTCTGTCTC(T)$_{20}$ (SEQ ID NO:5). Each of the 4 N's in P1 and P2 was a mixture of A, T, C, and G in equal ratios. Serum DNA of patient-L was extracted using a previously published method (Yeh et al. (2000) Hepatology 31, 1318). PCR was performed using random hexamers for 25 cycles and then any two of P1–3 primers. The resulting products were cloned into a vector, pCR2.1-TOPO (Invitrogen, Carlsbad, Calif.).

4. Elimination of Clones Containing Human Genomic Sequences

To eliminate clones containing human genomic sequences, all clones were lifted onto a nitrocellulose filter and hybridized with a mixture of probes generated from total liver RNA.

Briefly, single-stranded probes were generated from cytoplasmic RNA extracted from a normal human liver tissue. The tissue was minced into small pieces, and lysed in a buffer containing 10 mM Tris hydrochloride (pH 7.2), 150 mM NaCl, and 0.5% Nonidet® P-40. The lysate was centrifuged at 1500×g for 5 min and the supernatant was collected. Total RNA was extracted from the supernatant. Reverse transcription (RT) was performed using SuperScript® II RNase H minus Reverse Transcriptase (Invitrogen Corporation, Calsbad, Calif.) and oligo(dT) as the RT primer. One-third of dTTP in the dNTP mixture was replaced with digoxigenin-11-dUTP (Boehringer Mannheim, Germany) to generate digoxigenin-labeled probes. The probes were mixed (1:2 in molar ratio) with oligo(dA) at 40° C. for 1 hr before hybridization.

The hybridization signal was detected using a DIG Luminescent Detection Kit (Boehringer Mannheim, Germany). For each batch of hybridization, 1 ng of pDR2 without any cDNA insert was used as a negative control and 1 pg of pDR2 containing a fragment of human albumin gene (Hs.184411) was used as a positive control. The negatively hybridized clones were considered to contain sequences of non-human origin.

5. Automatic Sequencing

Clones containing sequences of non-human origin were subject to automatic DNA sequencing (CEQ 2000; Beckman Instruments, Inc., Fullerton, Calif.). The sequence data were further searched against the NCBI human genome data bank on the World Wide Web at ncbi.nlm.nih.gov/genome/seq/HsBlast.html to eliminate clones containing human sequences.

Results

1. Detection of a DNA Fragment of Non-Human Origin in Patient-L

A DNA fragment (Colon-V) containing an open reading frame with an incomplete 5' end was identified. This sequence is not present in the NCBI human genome data bank.

Four primers, Colon-VP1 to 4, were used for nested PCR. Colon-VP1 (nucleotides 106–125 of SEQ ID NO:1) and Colon-VP4 (complementary to nucleotides 281–300 of SEQ ID NO:1) were used for the first round PCR; Colon-VP2 (nucleotides 126–145 of SEQ ID NO:1) and Colon-VP3 (complementary to nucleotides 260–280 of SEQ ID NO:1) were used for the second round PCR. The results showed that the Colon-V sequence is not present in DNA extracted from HepG2 cells or human peripheral blood mononuclear cells from three different sources.

2. Detection of Colon-V Sequence in Patients by PCR

Serum samples from 5 groups of subjects were analyzed for the presence of the Colon-V sequence. The sequence was detected in 4% of healthy individuals, 0% of patients with chronic non-A-E hepatitis, 3% of patients with chronic hepatitis B, 0% of patients with chronic hepatitis C, and 25% of patients with colon cancer, respectively.

3. Colon-V is a DNA Molecule

Nucleic acid was extracted from the serum sample of patient-L using either a DNA or RNA extraction method. The nucleic acid was digested, respectively, with DNase I or RNase A before analysis by PCR. The results showed that Colon-V sequence is only present in the nucleic acid extracted using a DNA extraction method. Further, the Colon-V molecule is resistant to RNase A digestion but sensitive to DNase I digestion.

4. CsCl Gradient Analysis

A serum sample containing Colon-V sequence was used for CsCl gradient analysis. The serum was loaded on a 20–50% CsCl density gradient and centrifuged in a Beckman SW41 rotor at 38K rpm for 20 h. The gradients were then fractionated and analyzed for the presence of the Colon-V sequence (by one round of PCR). The PCR product was analyzed by electrophoresis and Southern blot. The Colon-V sequence was found in two fractions: the 1.23–1.26 g/ml fraction and the 1.18 g/ml fraction, suggesting that the Colon-V sequence belongs to a virus-like agent.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. An isolated nucleic acid comprising the nucleotide sequence of SEQ IS NO: 1, or the full complementary sequence thereof, wherein the presence of the nucleic acid in a subject predisposes the subject to an adenocarcinoma.

2. The nucleic acid of claim 1, wherein the adenocarcinoma is colon cancer.

3. A method of determining whether a subject is suffering from or at risk for developing an adenocarcinoma, the method comprising:

providing a sample from a subject; and detecting in the sample the nucleic acid of claim 1 wherein presence of said nucleic acid in the sample indicates that the subject is suffering from or at risk for developing an adenocarcinoma.

4. The method of claim 3, wherein the adenocarcinoma is colon cancer.

* * * * *